United States Patent
Siller Gonzalez et al.

(10) Patent No.: US 10,034,659 B2
(45) Date of Patent: Jul. 31, 2018

(54) URINE COLLECTION DEVICE FOR DEPENDENT PATIENTS

(71) Applicants: Andrea Siller Gonzalez, Nuevo Leon (MX); Adriana Torres Flores, Nuevo Leon (MX); Alicia De Hoyos Reyes, Nuevo Leon (MX); Ramses Galaz Mendez, Sonora (MX)

(72) Inventors: Andrea Siller Gonzalez, Nuevo Leon (MX); Adriana Torres Flores, Nuevo Leon (MX); Alicia De Hoyos Reyes, Nuevo Leon (MX); Ramses Galaz Mendez, Sonora (MX)

(*) Notice: Subject to any disclaimer, the term of this patent is extended or adjusted under 35 U.S.C. 154(b) by 309 days.

(21) Appl. No.: 14/890,724

(22) PCT Filed: Nov. 3, 2015

(86) PCT No.: PCT/MX2015/000142
§ 371 (c)(1),
(2) Date: Nov. 12, 2015

(87) PCT Pub. No.: WO2017/078508
PCT Pub. Date: May 11, 2017

(65) Prior Publication Data
US 2017/0252014 A1    Sep. 7, 2017

(51) Int. Cl.
*A61B 10/00* (2006.01)
*A61M 1/00* (2006.01)
*A61F 13/49* (2006.01)

(52) U.S. Cl.
CPC ............ *A61B 10/007* (2013.01); *A61F 13/49* (2013.01); *A61M 1/0031* (2013.01)

(58) Field of Classification Search
CPC .................................................... A61B 10/007
See application file for complete search history.

(56) References Cited

U.S. PATENT DOCUMENTS

| | | | | |
|---|---|---|---|---|
| 4,051,578 A | * | 10/1977 | Manschot | A61G 7/0503 24/130 |
| 4,972,844 A | * | 11/1990 | Cianci | A61B 5/14507 600/573 |
| 5,795,348 A | | 8/1998 | Roe et al. | |
| 8,382,734 B1 | | 2/2013 | Neuenschwander | |
| 2002/0091364 A1 | | 7/2002 | Prabhakar | |
| 2007/0088305 A1 | * | 4/2007 | Sakano | A61F 13/495 604/385.19 |

(Continued)

FOREIGN PATENT DOCUMENTS

| | | |
|---|---|---|
| CN | 201350148 | 11/2009 |
| ES | 1032931 | 7/1996 |

(Continued)

*Primary Examiner* — Michael C Stout
(74) *Attorney, Agent, or Firm* — Defillo & Associates; Evelyn A. Defillo

(57) ABSTRACT

The present invention provides a device that allows the collection of urine samples in patients who are not self-sufficient, providing a simple method to operate both for the patient and for the health personnel. The device is equipped with a primary collection system and a secondary collection system, which allows to obtain a complete sample of urine that can be transported for further analysis in the laboratory.

7 Claims, 8 Drawing Sheets

(56) References Cited

U.S. PATENT DOCUMENTS

| | | | | |
|---|---|---|---|---|
| 2010/0004612 A1* | 1/2010 | Thevenin | ................ | A61F 13/42 |
| | | | | 604/361 |
| 2010/0234820 A1* | 9/2010 | Tsai | ...................... | A61B 5/445 |
| | | | | 604/319 |
| 2011/0276020 A1 | 11/2011 | Mitsui | | |
| 2013/0123666 A1* | 5/2013 | Giuffrida | ............. | A61B 5/0024 |
| | | | | 600/595 |
| 2013/0296739 A1* | 11/2013 | Schultz | ................ | A61B 10/007 |
| | | | | 600/573 |

FOREIGN PATENT DOCUMENTS

| KR | 20070080196 | 8/2007 |
|---|---|---|
| WO | WO2015043400 | 4/2015 |

* cited by examiner

FIG. 5
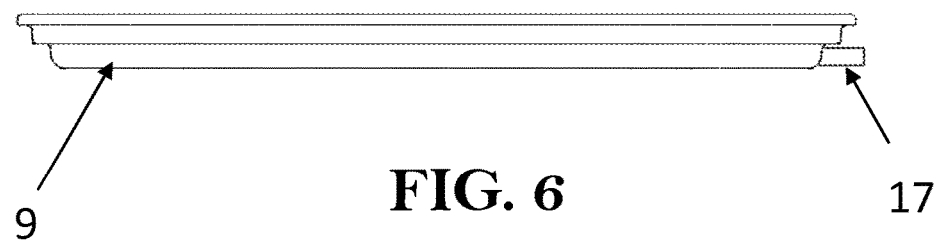
FIG. 6
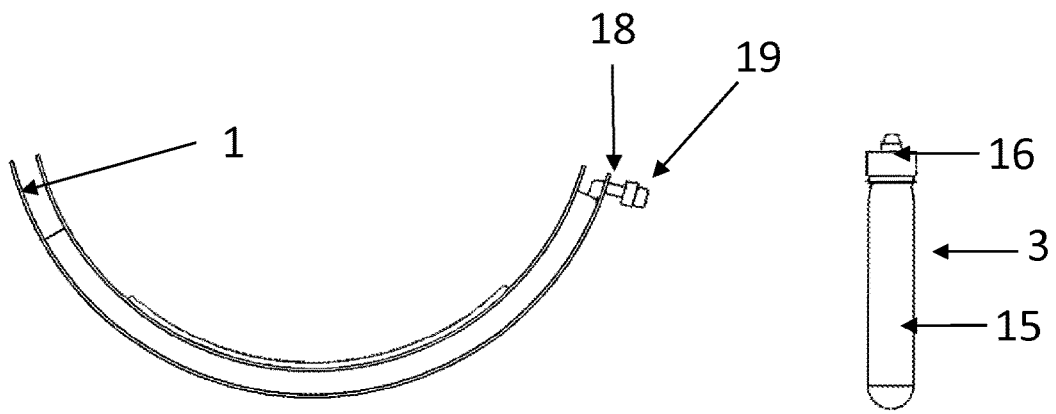
FIG. 7      FIG. 8

URINE COLLECTION DEVICE FOR DEPENDENT PATIENTS

CROSS REFERENCE TO RELATED APPLICATION

This application is a national stage entry of PCT/MX2015/000142 filed Nov. 3, 2015, under the International Convention.

DESCRIPTION

Object of the Invention

The object of the present invention is to provide a device that allows the collection of urine samples in patients who are not self-sufficient, providing a simple method to operate for the patient and the health personnel. The device is equipped with a primary collection system and a secondary collection system, which allows to obtain an entire urine sample that can be transported for further analysis in the laboratory.

BACKGROUND

The urinary system is made up by the kidneys, the bladder, and the urethra; its main function is to extract waste substances and water from the blood. The extracted substances which form the urine such as electrolytes (Na, K, Cl, $HCO_3$) and the products generated by the metabolic degradation of the proteins, such as urea, creatinine, sulphates, and phosphates, are transported by the ureters to temporary storage in the bladder, which has 400 to 500 ml of capacity.

The urine sample collection includes a series of steps that are performed to obtain a sample of it for a micro-biological analysis or any other type of test, the same way can contribute to the diagnosis determination and treatment or can serve to confirm the effectiveness of a particular medical treatment.

There are quantitative analysis that are carried out on samples representing excretions of urine over a 24-hour period; for this, it is necessary to start a collection after the first urination of the day preferably from 6:00 a.m. to 6:00 a.m. of the following day by using the proper technique.

Generally, the urine samples obtained at the patient's home are not properly collected, so the results are not completely reliable, and even more, if the patient is dependent, as an older adult or person with some kind of different ability or motor problem.

Therefore, in recent years a series of technologies has been developed that allows to improve the taking of urine samples for these patients, regardless of whether the sample is collected at home, resting residence, or hospital, however these technologies are based only on the urine collection for the convenience of the dependent patient and his caregiver, however they do not provide a means so that the urine can be stored and then later analyzed.

An example of these technologies is the Chinese Patent No. CN201350148Y, which describes a combined leak proof urine collector, which is manufactured through a combination of a paper diaper, a urine collection body, and a urine collection bag; the part of the head of the collector body is machined to be matched with the shape of the human body, and the rear end of the body is connected to a urine bag. A collector hole is located at the base of the paper diaper; by the use of connection pieces, the parts used for the fixing seat of the paper diaper are connected to the head part of the urine collector, the part of the seat of the paper diaper surrounds the outside of the head part of the urine collector body, and it is connected with the part of the head of the urine collector body so that the part of the head of the urine collector body is fixed on the outside of the human body through the paper diaper.

Both the Korean application KR20070080196, the Spanish utility model number ES1032931U, and U.S. Pat. No. 5,795,348 provide diapers for adults, which although they do not apply specifically for the urine collection specifically for the taking of medical samples, due to its technical relevance are being cited within this patent application in order to have a broader vision of the State of the art related to the technical field, so below.

The detailed technology in the document KR20070080196 focuses on reducing the environmental pollution and allows the patient, who has urinary incontinence or diseases, to use in an economical way since the urine is discharged directly, maintaining the comfort even when it is repeatedly used. The adult diaper includes: a collection body with a shape of a container which has a space formed inside and an opening hole formed in a top portion by a cut, and has a fixed hose attached to lower portion and extended towards the outside. It also includes a primary detachable member on the lower portion; and a main body formed by a pad or a panty form, that has a detachable secondary member located on the top portion for the connection with the primary detachable member of the collection body.

Another related document is the ES1032931U which includes a diaper with a collection bag to collect the feces, an independent exit for the urine, and a hole that provides passage to the progenitor organs, also is claimed a female urine collector, made of latex, with semi-spherical shape and self-adhesive opening which should be placed in the labia of the women and which is provided with a discharge tube for the urine.

In the same way the U.S. Pat. No. 5,795,348 discloses a disposable absorbent article such as a diaper, which has a top layer, a rear layer, and a middle nucleus; attached to the surface and oriented away from the top layer is located a spacer ejector. The spacer receives and collects the fecal material and the urine from the user. The spacer can be extracted from the diaper, or can be articulated in relation to the diaper. When the spacer is expelled from the diaper, the fecal material and urine can be easily thrown in the toilet, and not discarded in a regular trash can, where it represents a health hazard.

Another U.S. Pat. No. 8,382,734B1, discloses a diaper with a primary component that is formed by a flexible sheet that has a periphery and a central opening, an exterior receiving area, and an interior surface with an adhesive to be detachable attached to a user with the central opening about the same, the recipient has a chamber and an opening to receive and collect the fecal material and the urine, and an intermediate element has a separable closure to independently connect the container with the primary component.

In the same way, the US2002091364A1 patent application, provides an external urine draining system suspended that includes a barrier to liquids with a peripheral connected to a collector and a tubular cross-section, which surrounds the barrier. A plurality of capillary tubes pass through a wall of the collector. Each of the plurality of capillaries tubes has an entrance adjacent to the liquid barrier and a capillary discharge exit inside the collector, every capillary tube is covered by a soft lining. Discharge tubes connected to the collector carry urine to a bag of holding.

In addition, the US2011276020A1 application discloses an improved article for the treatment of body fluid in order to ensure that body fluids do not escape particularly when the user's body weight is exerted on it or there are posture changes, also includes a clothing article that includes the same. The article for the treatment of body fluid is attached to a diaper that features a coating on the body side and a backing sheet before the diaper, forming an opening that extends in a direction of the thickness of them. A liquid absorbent core or a liquid absorbent structure is added with a liquid guide opening that extends through the same to be centrally aligned with the opening. The opening of the container is exposed on the side which is oriented towards the body of the user through the liquid guide opening and in front of the external genitals of the user.

The international application number WO2015043400A1 discloses a diaper with a urine collection device, provided with an opening for the installation of a urine collection device in a position corresponding to the organ of urination of the human body; the diaper is equipped with a fixation component that is placed surrounding the part of the waist and the opening of the diaper in order to adjust the position of the urine collection device, while tied to the waist part of the diaper. When using the diaper with the urine collection device, a patient can conveniently adjust the position of the urine collection device, while tying the diaper to the waist by simply tying a single long cable, so that the urine collection device conforms completely to the organ of urination of the patient and prevents the urine leak.

The above mentioned technologies provide different diapers and urine collection devices, either to avoid leakage or attach properly to the patient's body, channeling the urine to a secondary container or containing itself their own urine container, however none of them is used for taking medical samples on dependent patients. So, the novelty of the present invention lies at this point, the fact of providing a device capable of collecting clean urine samples allowing to be coupled to dependent patients, allowing simultaneously the right collection for subsequent analysis and above all avoiding the disadvantages of sampling of urine in patients in particular, so caregivers or nurses responsible for them can perform this routine practice with less effort and less discomfort for the dependent patient.

BRIEF DESCRIPTION OF THE FIGURES

FIG. 5 illustrates a left lateral view of the primary collector system of the urine sample collecting device for dependent patients.

FIG. 6 illustrates a right lateral view of the primary collector system of the urine sample collecting device for dependent patients.

FIG. 7 illustrates a right side view of the collector device of the present invention, assembled in a diaper taking curvature characteristic of the same.

FIG. 8 illustrates a front view of the collection container charged with negative pressure.

DETAILED DESCRIPTION OF THE INVENTION

Figure 13:
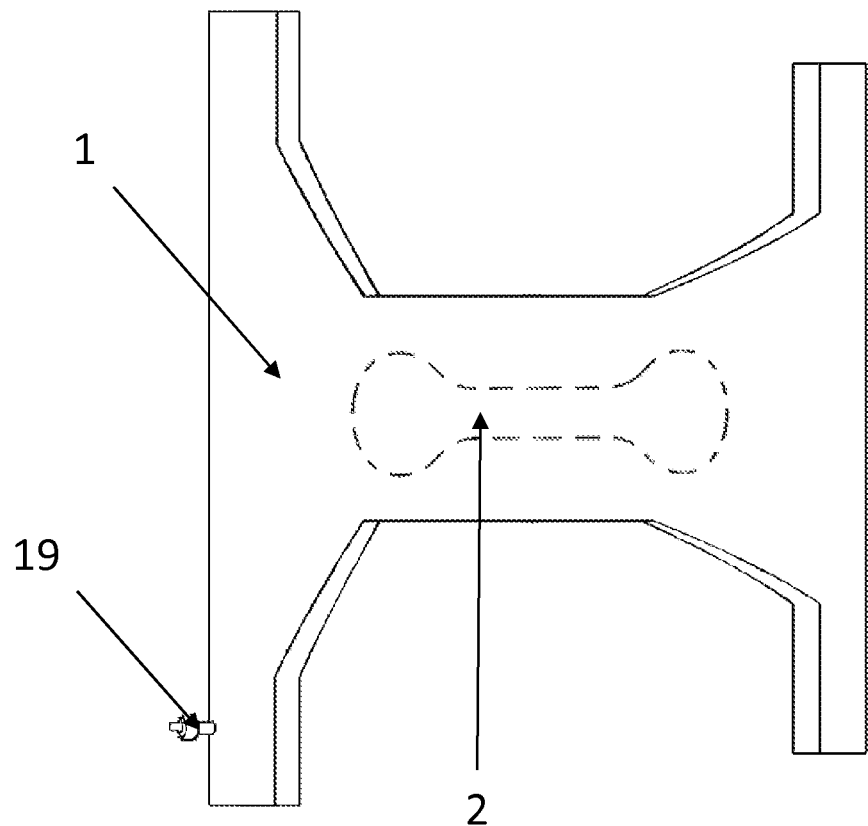
FIG. 13 illustrates a bottom view of the collector device of the present invention assembled in a diaper in an open position.
Figure 14:
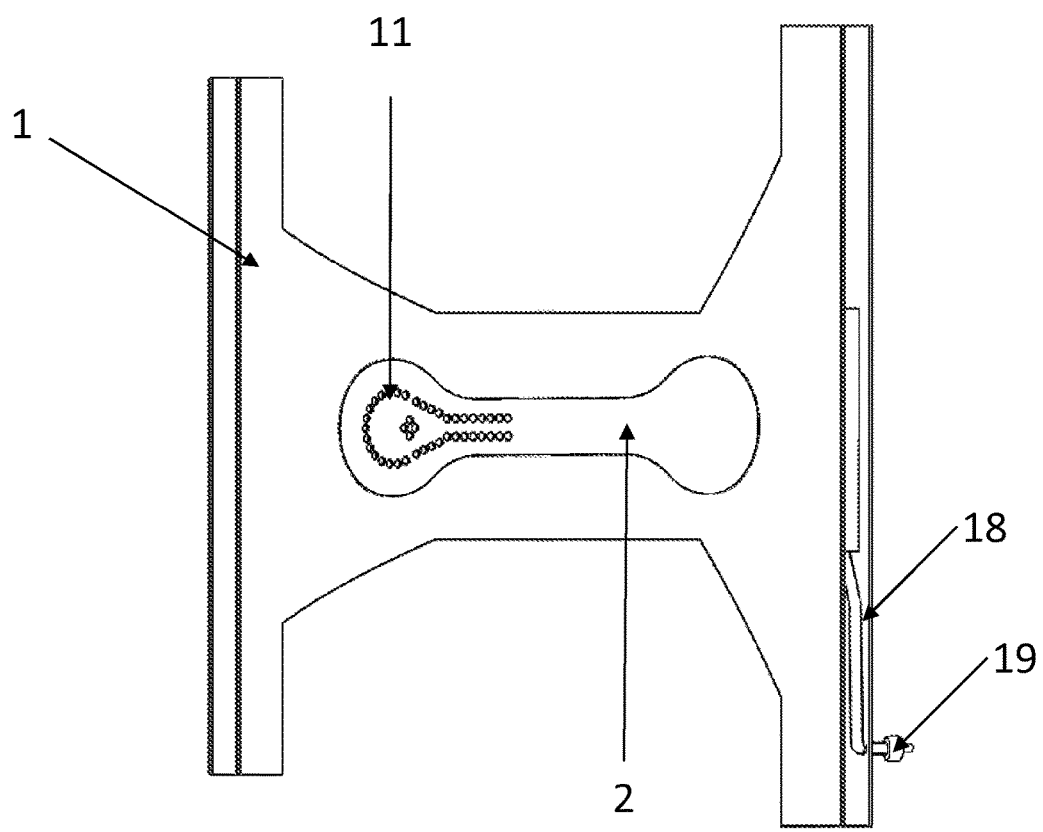
FIG. 14 illustrates a top view of the device assembled in a diaper in open position showing the location of the primary collector system and the distribution of the top holes.

The present invention comprises a device designed to collect urine samples in patients who are not self-sufficient. The device is assembled within the structure of a regular diaper (1), specific and preferably so that the device occupies the central area of the diaper and leaving around the device areas of absorption in the diaper (1), which prevent leaks, in the same way the assembled between the diaper (1) and the device allows that the top surface of the diaper (1) as well as the top surface of the primary collector system to be at the same height forming a flat absorbent surface, as can be seen in FIG. 7, which avoids inconvenience to the patient at the time of wearing the diaper with the device; the diaper is illustrated in FIG. 13 and FIG. 14.

Figure 1:
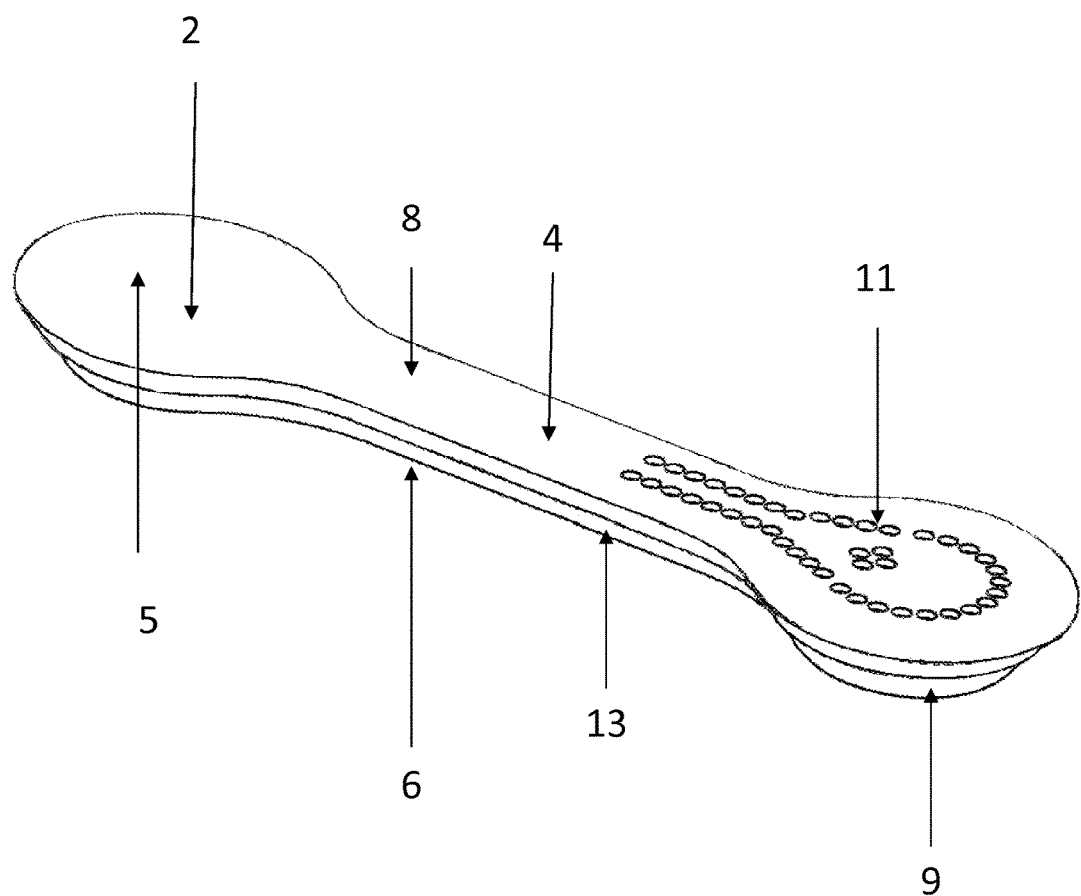
FIG. 1 illustrates an isometric view of the primary collector system of the urine sample collecting device for dependent patients, where it can be seen the configuration of the plurality of top holes.
Figure 2:
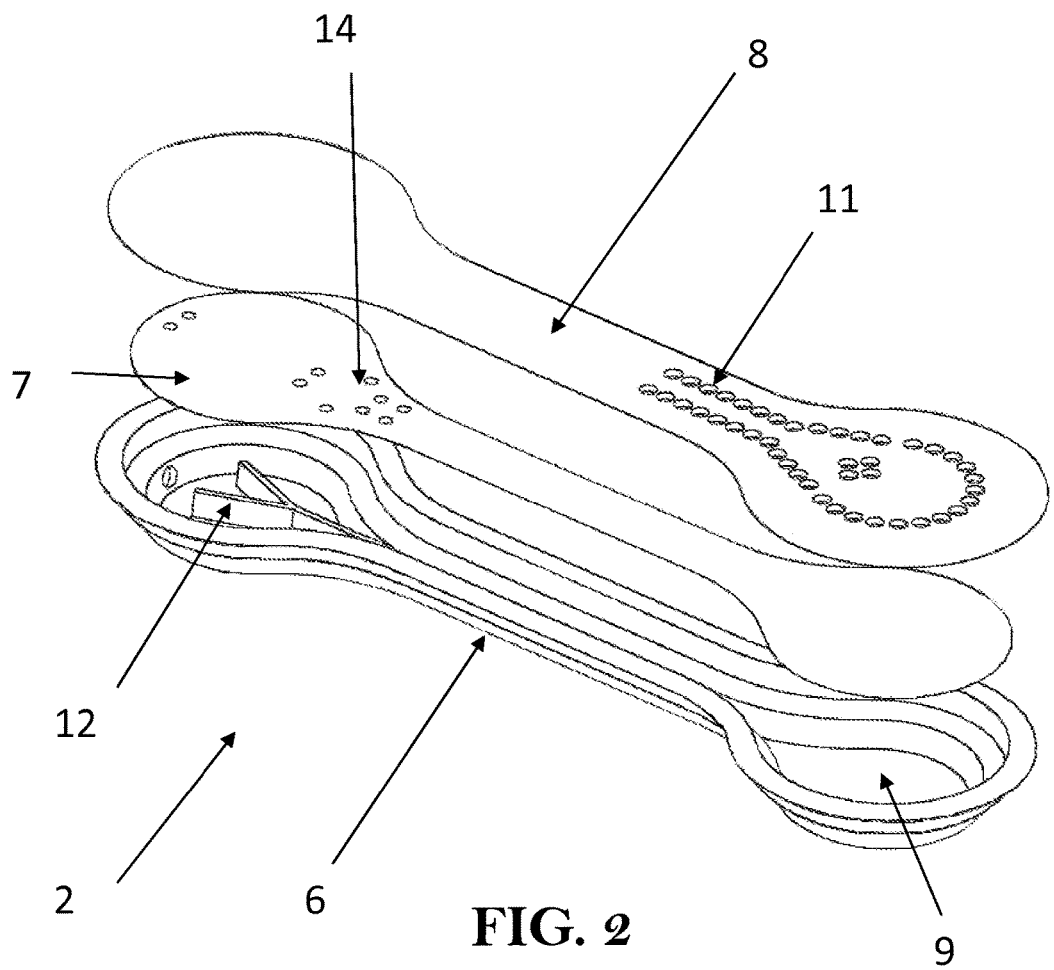
FIG. 2 illustrates an isometric exploded view of the primary collector system of the urine sample collecting device for dependent patients showing in detail the three layers that make up the collector.
Figure 3:
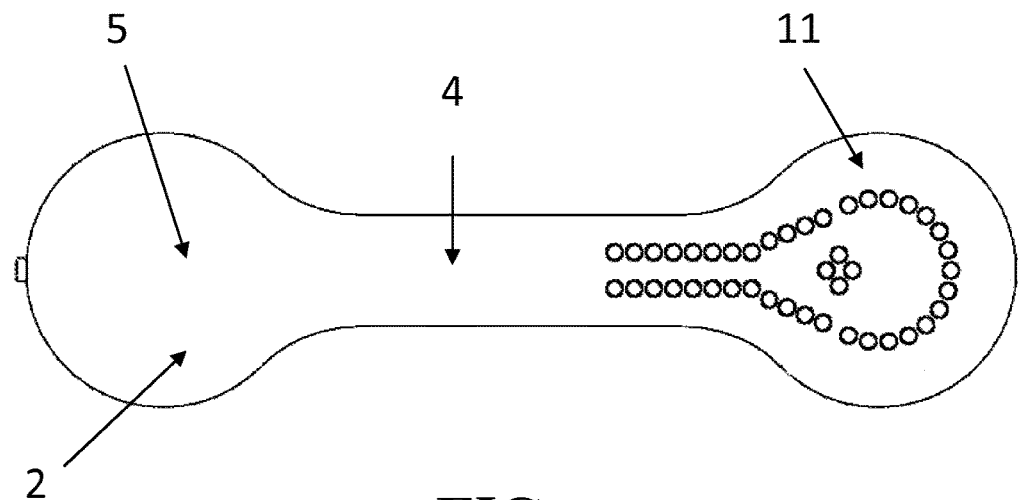
FIG. 3 illustrates a top view of the primary collector system of the present invention, showing the distribution of the plurality of top holes.
Figure 4:
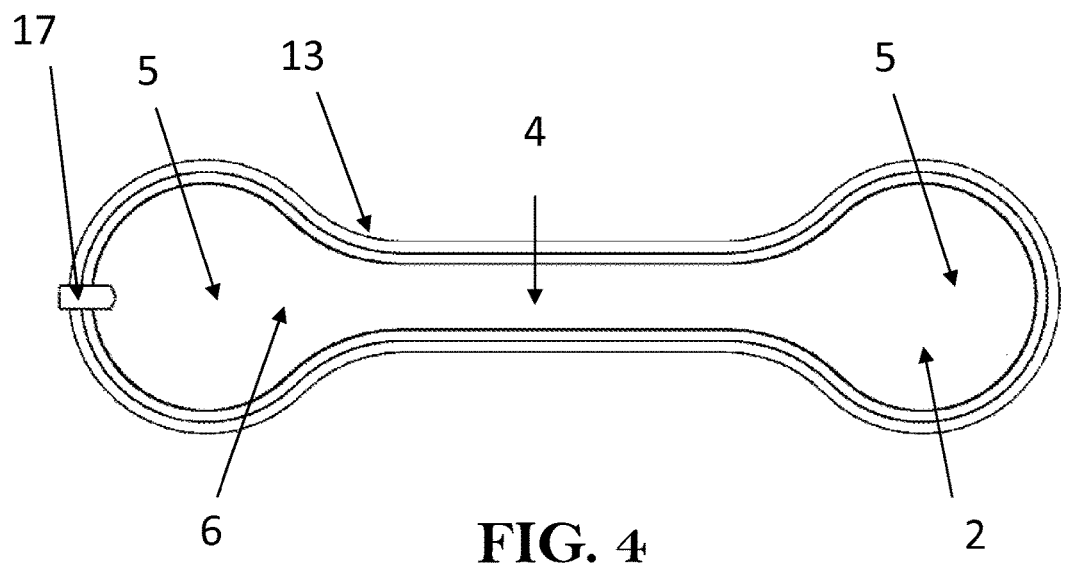
FIG. 4 illustrates a bottom view of the primary collector system of the present invention showing the pyramidal distribution of the peripheries of the layers.
Figure 9:
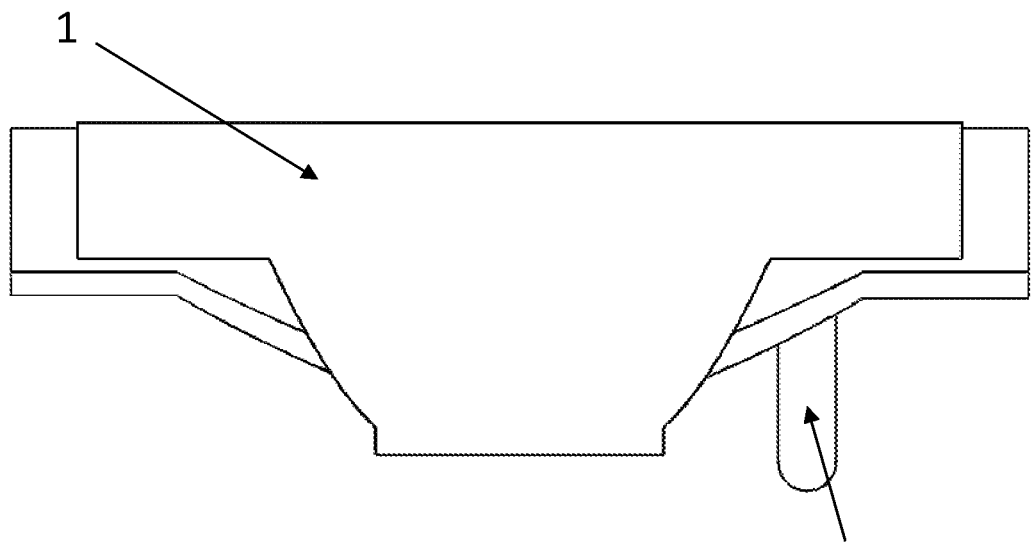
FIG. 9 illustrates a front view of the device assembled in a diaper in closed position.
Figure 10:
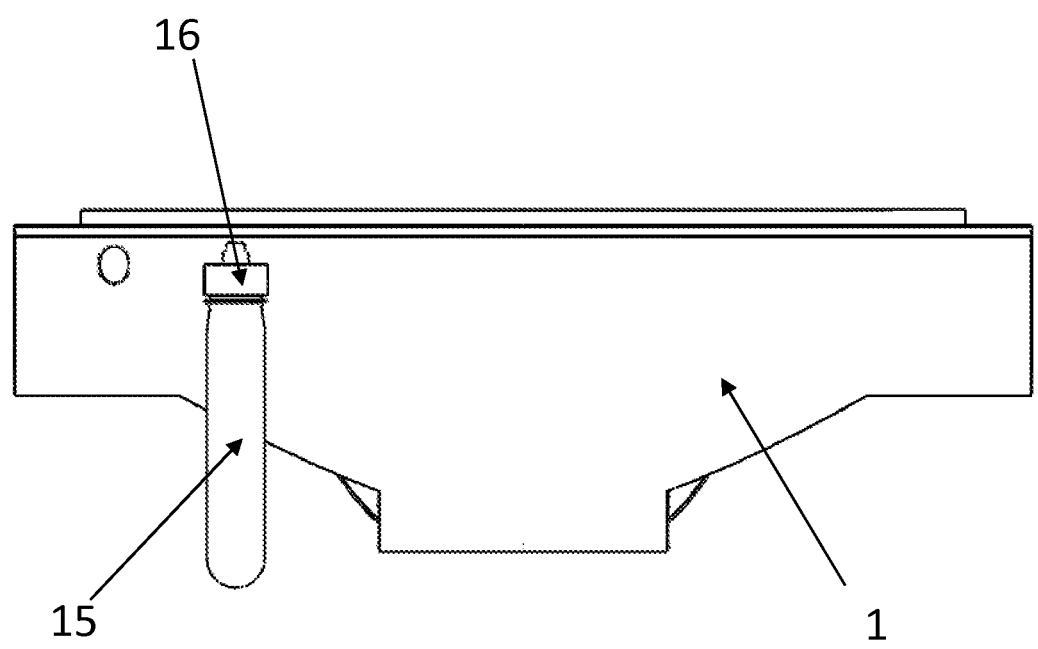
FIG. 10 illustrates a rear view of the device of the present invention assembled in a diaper in closed mode.

The device comprises two main systems: a primary collector system (2), shown in FIG. 1, and a secondary collector system (3). The primary collector system (2) includes a flat containing vessel and elongated with a geometry in its main structure having an 8shape, as shown in FIG. 3 and FIG. 4, which comprises an elongated main body (4) in its center and each end of the main body has a semicircular bend (5) at their edges, the length and thickness of the elongation in the central part of the containing vessel is thin enough to be able to be placed in the crotch of the patient, the thickness is shown in FIG. 5 and FIG. 6. The containing vessel includes three layers of flexible plastic, shown in FIG. 2, preferably PVC plastic, which provides a certain degree of flexibility for the correct adaptation to the curvature of the diaper. The layers include a primary lower layer (6), an intermediate secondary layer (7), and an upper tertiary layer (8). These layers are structured in parallel and equidistant way to each other, connected by their outer edges so that between the primary lower layer (6) and the secondary intermediate layer (7) it is formed a first collection chamber (9) and between the intermediate secondary layer (7) and the upper tertiary layer it is formed a second collection chamber (10), the outer edges are preferably assembled to the primary lower layer (6) as shown in FIG. 2, both of the first collection chamber (9) and the second collection chamber (10) have an adequate space for circulating the urine between them.

The first collection chamber (9) captures the urine once the urination is made, while on the surface of the second collection chamber (10), i.e. on the exterior part of the upper tertiary layer (8) presents a plurality of holes (11) having a specific pattern and geometry, these plurality of holes (11) has a rectilinear main distribution which follows the internal periphery of the upper geometry of the primary collection system (2) and this rectilinear distribution only covers the front part of the primary collection system (2), i.e. the part that is in contact with the urination organ of the patient, which allows the plurality of holes (11) to act as an entry of urine to the primary collection system (2), by the filtration of urine in only one direction. Inside the first collection chamber (9) and fixed to the inside of the primary lower layer (6) and the secondary intermediate layer (7), a Y-shaped structure (12) is located that provides structural support to the primary collection system (2), in such a way to avoid the collapse once the patient's weight is applied to the two chambers.

Figure 11:
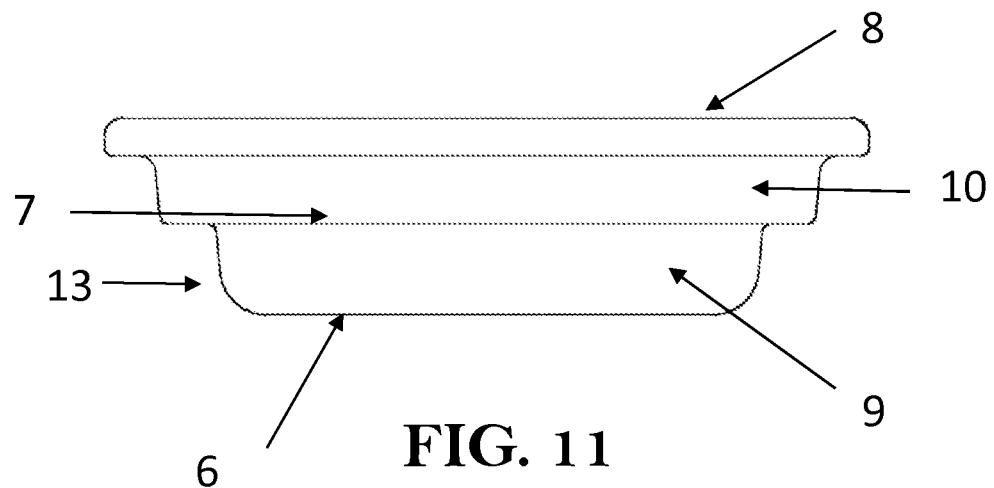
FIG. 11 illustrates a front view of the primary collector system showing the distribution of the edges of the three layers.
Figure 12:
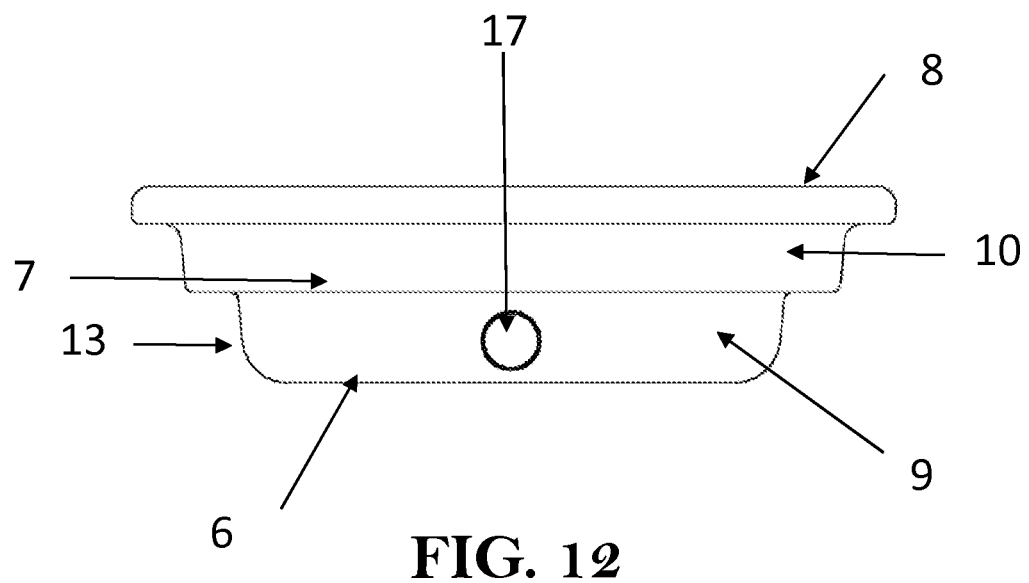
FIG. 12 illustrates a rear view of the primary collector system showing the hole for the attachment of the flexible hose.

The surface of each layer is less with respect to the top layer, by which the primary collection system (2) presents an invert stepped structure in its periphery (13), as shown in FIG. 11 and FIG. 12.

The first collection chamber (9) and the second collection chamber (10) are communicated through at least one conductor hole (14), preferably a plurality of conductor holes, located between the elongated main body (4) and the end of the main body which has a semicircular bend (5), the plurality of conductor holes (14) are located in the secondary intermediate layer (7) specifically on the opposite end to the location of the plurality of holes (11), so that the urine does not leave the primary collector system (2).

In the same way the primary collector system (2) is wrapped in a non-woven fabric in such a way that the contact of the device with the patient's skin is comfortable.

The secondary collector system (3) comprises a collection container (15) with an input, as shown in FIG. 8, which is loaded with negative pressure, the container (15) includes a hermetically sealed device (16) that prevents leak of the vacuum, said hermetically sealed device (16) is preferably a plug located at the entrance of the same, in the same input of the container (15) and includes an adaptation valve that is normally closed.

In the back side of the first chamber is located an output hole (17) on which is connected a flexible hose (18), the hose (18) is the union between the secondary collector system (3) and the primary collector system (2), since the end of the hose that is opposite to the end in the hole, is connected to the valve of the secondary collector system (3).

Immediately from outlet (17) and connected to the hose (18), is located at least one component (19) that allows to activate the collection system in a manual, automatic or semi-automatic way. Depending on the type of collection, said component may be but is not limited to: a valve with a mouth and shutoff type luer (valve lock luer) with a stopper that prevents the exit of the urine, a sheet or hydro soluble plug that works by blocking the proximal outlet of the hose and when is dissolved on contact with the urine activates the collection system, a nitinol wire that changes its structure with the contact with fluids of higher temperature and activates the system, and a clamp or hook that presses the hose, and are then released to activate the system.

USE OF THE INVENTION

Once the patient urinates, the urine is contained in the primary collector system (2). To activate the collection system (3) it is necessary to adapt the component (19) of the hose (18) with the normally closed valve of the vacuum container. This mechanism will allow the free passage through the valve normally closed so the vacuum suctions the sample contained in the primary collector system (2) through the hose (18) into the container (15). Then the hose (18) is disconnected, the diaper (1) may be discarded and the sample is contained in the container (15). The container (15) can be transported conveniently to the place where it can be analyzed, so that the laboratory personnel unscrews the cap from the container to access and make use of the urine sample.

Having described enough my invention, consider it as a novelty and therefore claim as my exclusive property, contained in the following clauses.

The invention claimed is:

1. A urine sample collecting device for dependent patients comprising:
    a primary collector system;
    a secondary collector system;
    the primary collector system includes:
    a flat and elongated containing vessel having an eight shape and including a first end, a center part, a second end, the second end is opposite to the first end, an elongated main body is located at the center part of the elongated containing vessel, the first end and the second end have a semicircular shape;
    a primary lower layer;
    a secondary intermediate layer, and
    upper tertiary layer; the primary, secondary, and tertiary layers are located parallel to each other and connected at their outer edges;
    a first collection chamber is formed between the connection of the lower primary layer and the secondary intermediate layer;
    a second collection chamber is formed between the connection of the secondary intermediate layer and the top tertiary layer;
    the upper tertiary layer includes a plurality of holes located on the second end of the elongated containing vessel, the plurality of holes present a rectilinear distribution that follows an inner periphery of the primary collection system, the rectilinear distribution covers a front part of the primary collection system;
    a structure having a Y-shape is located inside the first collection chamber, the structure is attached to an internal part of the primary lower layer and the secondary intermediate layer,
    at least one conductor hole is located on the intermediate secondary layer between the elongated main body and the first end of the main body, the plurality of holes of the upper tertiary layer are located opposite to the at least one conductor hole of the intermediate secondary layer, the at least one conductor hole connects the first collection chamber and the second collection chamber;
    the secondary collector system comprises a collection container loaded with negative pressure, the collection container includes an input port and a valve connected to the input;
    an output hole is located at a back end of the first chamber;
    a flexible hose connected to the output hole;
    an activation device connected to the flexible hose;
    wherein the urine sample collecting device is assembled inside a central area of a regular diaper leaving around the urine sample collecting device absorption zones for the diaper, a top surface of the diaper and an external side of the upper tertiary layer are the same height.

2. A urine sample collecting device for dependent patients comprising:
    a primary collector system;

a secondary collector system;

the primary collector system includes a flat and elongated containing vessel having an eight shape and including a first end, a center part, a second end, the second end is opposite to the first end, an elongated main body is located at the center part of the elongated containing vessel, the first end and the second end has a semicircular shape;

the elongated containing vessel includes a primary lower layer, a secondary intermediate layer, and upper tertiary layer; the layers are located parallel to each other, the layers are connected at their outer edges;

a first collection chamber is formed between the connection of the lower primary layer and the secondary intermediate layer;

a second collection chamber is formed between the connection of the secondary intermediate layer and the top tertiary layer;

the upper tertiary layer includes a plurality of holes located on the second end of the elongated containing vessel, the plurality of holes present a rectilinear distribution that follows an inner periphery of the primary collection system, the rectilinear distribution covers a front part of the primary collection system;

a structure having a Y-shape is located inside the first collection chamber, the structure is attached to an internal part of the primary lower layer and the secondary intermediate layer, at least one conductor hole is located on the intermediate secondary layer between the elongated main body and the first end of the main body, the at least one conductor hole connects the first collection chamber and the second collection chamber;

the secondary collector system comprises a collection container loaded with negative pressure, the collection container includes an input port and a valve connected to the input;

an output hole is located at a back end of the first chamber;

a flexible hose connected to the output hole;

an activation device connected to the flexible hose;

wherein the primary lower layer, the secondary intermediate layer, and the upper tertiary layer are made of a flexible plastic;

wherein the flexible plastic is polyvinyl chloride.

3. The urine sample collecting device for dependent patients according to claim 1, wherein the first collection chamber and the second collection chamber include a space for the urine to circulate between them to avoid the urine back and forward and just moving in one direction.

4. A urine sample collecting device for dependent patients comprising:

a primary collector system;
a secondary collector system;
the primary collector system includes:
a flat and elongated containing vessel having an eight shape and including a first end, a center part, a second end, the second end is opposite to the first end, an elongated main body is located at the center part of the elongated containing vessel, the first end and the second end has a semicircular shape;

a primary lower layer,
a secondary intermediate layer, and
an upper tertiary layer; the primary, secondary, and tertiary layers are located parallel to each other and connected at their outer edges;

a first collection chamber is formed between the connection of the lower primary layer and the secondary intermediate layer;

a second collection chamber is formed between the connection of the secondary intermediate layer and the top tertiary layer;

the upper tertiary layer includes a plurality of holes located on the second end of the elongated containing vessel, the plurality of holes present a rectilinear distribution that follows an inner periphery of the primary collection system, the rectilinear distribution covers a front part of the primary collection system;

a structure having a Y-shape is located inside the first collection chamber, the structure is attached to an internal part of the primary lower layer and the secondary intermediate layer, at least one conductor hole is located on the intermediate secondary layer between the elongated main body and the first end of the main body, the plurality of holes of the upper tertiary layer are located opposite to the at least one conductor hole of the intermediate secondary layer, the at least one conductor hole connects the first collection chamber and the second collection chamber;

the secondary collector system comprises a collection container loaded with negative pressure, the collection container includes an input port and a valve connected to the input;

an output hole is located at a back end of the first chamber;

a flexible hose connected to the output hole;

an activation device connected to the flexible hose;

wherein the urine sample collecting device is assembled inside a central area of a regular diaper leaving around the urine sample collecting device absorption zones for the diaper, a top surface of the diaper and an external side of the upper tertiary layer are the same height;

wherein each layer has a surface that is less than a surface of the upper tertiary layer by which the primary collection system features an inverted stepped structure in the periphery.

5. The urine sample collecting device for dependent patients according to claim 1, wherein the primary collector system is wrapped in a woven or a nonwoven fabric.

6. The urine sample collecting device for dependent patients according to claim 1, further including a hermetically sealed device connected to the secondary collection system.

7. The urine sample collecting device for dependent patients according to claim 1, wherein the activation device is selected from the group consisting of a luer lock valve, a cap, a sheet, a hydro-soluble plug, and a nitinol wire.

* * * * *